US012734319B2

(12) United States Patent
Zhao et al.

(10) Patent No.: US 12,734,319 B2
(45) **Date of Patent: *Sep. 15, 2026**

(54) RESPIRATION AIDING EQUIPMENT

(71) Applicants: VINCENT MEDICAL (DONG GUAN) MANUFACTURING CO., LTD, Dongguan (CN); VINCENT MEDICAL (DONG GUAN) TECHNOLOGY CO., LTD, Dongguan (CN)

(72) Inventors: Jun Zhao, Dongguan (CN); Jixiang Tao, Dongguan (CN); Jiebing Xu, Dongguan (CN); Haibin Yu, Dongguan (CN)

(73) Assignees: VINCENT MEDICAL (DONG GUAN) MANUFACTURING CO., LTD, Dongguan (CN); VINCENT MEDICAL (DONG GUAN) TECHNOLOGY CO., LTD, Dongguan (CN)

( * ) Notice: Subject to any disclaimer, the term of this patent is extended or adjusted under 35 U.S.C. 154(b) by 947 days.

This patent is subject to a terminal disclaimer.

(21) Appl. No.: 17/802,025

(22) PCT Filed: Jul. 16, 2021

(86) PCT No.: PCT/CN2021/106698

§ 371 (c)(1),
(2) Date: Aug. 24, 2022

(87) PCT Pub. No.: WO2022/257227

PCT Pub. Date: Dec. 15, 2022

(65) Prior Publication Data

US 2023/0355904 A1 Nov. 9, 2023

(30) Foreign Application Priority Data

Jun. 8, 2021 (CN) ......................... 202110639612.5

(51) Int. Cl.
*H02H 9/00* (2006.01)
*A61M 16/00* (2006.01)
(Continued)

(52) U.S. Cl.
CPC .... *A61M 16/0087* (2013.01); *A61M 16/1095* (2014.02); *H02H 3/08* (2013.01);
(Continued)

(58) Field of Classification Search
CPC .. A61M 16/0087; A61M 16/1095; H02H 3/08
(Continued)

(56) References Cited

U.S. PATENT DOCUMENTS

2002/0158609 A1* 10/2002 Lavington ........... H02J 7/00309 320/165
2009/0109591 A1 4/2009 Li et al.
(Continued)

FOREIGN PATENT DOCUMENTS

CN 201754505 U 3/2011
CN 202034757 U 11/2011
(Continued)

*Primary Examiner* — Crystal L Hammond
*Assistant Examiner* — Lucy M Thomas
(74) *Attorney, Agent, or Firm* — MUNCY, GEISSLER, OLDS & LOWE, P.C.

(57) ABSTRACT

Respiration aiding equipment is provided, wherein the respiration aiding equipment includes a main control module, a heating loop and a heating loop protective circuit connected to the heating loop, and the heating loop protective circuit includes an acquisition sub-circuit, a suppression sub-circuit, a protective sub-circuit and a discharge sub-circuit; the acquisition sub-circuit collects input voltage of the protective sub-circuit and sends the input voltage to the suppression sub-circuit; the suppression sub-circuit clamps the input voltage and releases current through the discharge sub-circuit; and the protective sub-circuit performs short-
(Continued)

circuit protection when the current is too high. In the present disclosure, the over-voltage protection is realized through the voltage clamp in such a manner of monitoring the voltage of the heating loop and suppressing the input voltage through the suppression sub-circuit, and then the over-current protection is realized through the protective sub-circuit when the circuit current is too high.

11 Claims, 3 Drawing Sheets

(51) Int. Cl.
*A61M 16/10* (2006.01)
*H02H 3/08* (2006.01)

(52) U.S. Cl.
CPC ............... *A61M 2205/3368* (2013.01); *A61M 2205/6027* (2013.01)

(58) Field of Classification Search
USPC ........................................................... 361/56
See application file for complete search history.

(56) References Cited

U.S. PATENT DOCUMENTS

| | | | | |
|---|---|---|---|---|
| 2010/0214707 | A1* | 8/2010 | Yun ....................... | H02J 7/0031 361/92 |
| 2014/0216459 | A1 | 8/2014 | Vos et al. | |
| 2016/0334815 | A1* | 11/2016 | Chen .................... | H05B 1/0272 |
| 2020/0306489 | A1* | 10/2020 | Wright .................. | A61M 16/16 |

FOREIGN PATENT DOCUMENTS

| | | | | |
|---|---|---|---|---|
| CN | 103121409 | A | | 5/2013 |
| CN | 104597823 | A | | 5/2015 |
| CN | 205724875 | U | | 11/2016 |
| CN | 209187820 | U | | 8/2019 |
| CN | 111342641 | A | | 6/2020 |
| JP | H06139916 | A | * | 5/1994 |

* cited by examiner

RESPIRATION AIDING EQUIPMENT

TECHNICAL FIELD

The present disclosure relates to the technical field of circuits, in particular to respiration aiding equipment.

BACKGROUND

The existing respiration aiding equipment (such as a respirator) is usually provided with a variety of pipelines, and each pipeline is provided with an identification element and a temperature detection circuit. The respiration aiding equipment identifies pipeline information through the identification element, and temperatures of an air inlet and an air outlet of the pipeline are detected through the temperature detection circuit, and then the corresponding respiration working mode is carried out.

However, due to reversely or wrongly connected circuit or high instantaneous voltage when powering on and other situations, a heating loop of the existing respiration aiding equipment will occur leakage touch spark during use, resulting in a great safety risk.

Therefore, the prior art still needs to be improved and enhanced.

SUMMARY

The purpose of the present disclosure is to provide respiration aiding equipment, which can effectively avoid the safety risk caused by instantaneous high voltage touched electric spark.

In order to achieve the above purpose, the present disclosure adopts the technical solution below:

Respiration aiding equipment, including a main control module, a heating loop and a heating loop protective circuit connected to the heating loop, and the heating loop protective circuit includes an acquisition sub-circuit, a suppression sub-circuit, a protective sub-circuit and a discharge sub-circuit; the acquisition sub-circuit collects input voltage of the protective sub-circuit and sends the input voltage to the suppression sub-circuit; the suppression sub-circuit clamps the input voltage and releases current through the discharge sub-circuit; and the protective sub-circuit performs short-circuit protection when the current is too high.

In the respiration aiding equipment, the acquisition sub-circuit includes a first diode, a second diode and a third diode; an input end of the first diode, an input end of the second diode and an input end of the third diode are connected to the protective sub-circuit, and collect first input voltage, second input voltage and third input voltage respectively; and an output end of the first diode, an output end of the second diode and an output end of third diode are connected to the suppression sub-circuit.

In the heating loop protective circuit, the protective sub-circuit includes:

a first protective unit for performing short-circuit protection on a heating wire;

a second protective unit for performing short-circuit protection on a temperature detection module of the heating loop;

a third protective unit for performing short-circuit protection on the discharge sub-circuit;

one end of the first protective unit is connected to an input end of the heating wire, the other end of the first protective unit is accessed to a first power source, one end of the second protective unit is connected to the acquisition sub-circuit and accessed to input voltage, the other end of the second protective unit is connected to the temperature detection module and an identification module of the heating loop, one end of the third protective unit is connected to the suppression sub-circuit, and the other end of the third protective unit is connected to the discharge sub-circuit.

In the respiration aiding equipment, the main control module includes a first protective unit for performing the short-circuit protection on the heating wire, one end of the first protective unit is connected to an output end of the power source, and the other end of the first protective unit is connected to an input end of the power source.

In the respiration aiding equipment, the protective sub-circuit includes a second protective unit for performing the short-circuit protection on the temperature detection module of the heating loop, and a third protective unit for performing the short-circuit protection on the discharge sub-circuit; one end of the second protective unit is connected to the acquisition sub-circuit and accessed to the input voltage, the other end of the second protective unit is connected to the temperature detection module and the identification module of the heating loop, one end of the third protective unit is connected to the suppression sub-circuit, and the other end of the third protective unit is connected to the discharge sub-circuit.

In the respiration aiding equipment, the first protective unit includes a first resistance and a first fuse; and one end of the first fuse is connected to one end of the first resistance, the other end of the first fuse is connected to the input end of the heating wire, and the other end of the first resistance is connected to an anode of a first power source.

In the respiration aiding equipment, the first protective unit includes a second resistance and a second fuse; and one end of the second fuse is connected to one end of the second resistance, the other end of the second fuse is connected to the output end of the power source, and the other end of the second resistance is connected to the input end of the power source.

In the respiration aiding equipment, the second protective unit includes a first protective tube, a second protective tube and a third protective tube; one end of the first protective tube is connected to the input end of the first diode and accessed to first input voltage; the other end of the first protective tube is connected to the temperature detection module; one end of the second protective tube is connected to the input end of the second diode and accessed to second input voltage; the other end of the second protective tube is connected to the temperature detection module; one end of the third protective tube is connected to the input end of third diode and accessed to third input voltage; and the other end of the third protective tube is connected to the identification module.

In the respiration aiding equipment, the first fuse is a self-recovery fuse.

In the respiration aiding equipment, the second fuse is a self-recovery fuse.

Compared with the prior art, the present disclosure provides respiration aiding equipment, wherein the respiration aiding equipment includes the main control module, the heating loop and the heating loop protective circuit connected to the heating loop, and the heating loop protective circuit includes the acquisition sub-circuit, the suppression sub-circuit, the protective sub-circuit and the discharge sub-circuit; the acquisition sub-circuit collects the input voltage of the protective sub-circuit and sends the input voltage to the suppression sub-circuit; the suppression sub-circuit clamps the input voltage and releases the current through the discharge sub-circuit; and the protective sub-circuit performs short-circuit protection when the current is too high. In the present disclosure, the over-voltage protection is realized through the voltage clamp in such a manner of monitoring the voltage of the heating loop and suppressing the input voltage through the suppression sub-circuit, and then the over-current protection is realized through the protective sub-circuit when the circuit current is too high, thereby avoiding the safety risk caused by instantaneous high voltage touched electric spark.

DETAILED DESCRIPTION OF THE EMBODIMENTS

The purpose of the present disclosure is to provide respiration aiding equipment, which can effectively avoid the safety risk caused by instantaneous high voltage touched electric spark.

In order to make the objectives, technical solution and effects of the present disclosure clearer and definer, the embodiments of the present disclosure will be described in detail below in conjunction with the drawings. It is understood that the specific embodiments described herein are merely used for explaining the present disclosure, instead of limiting the present disclosure.

Figure 1:
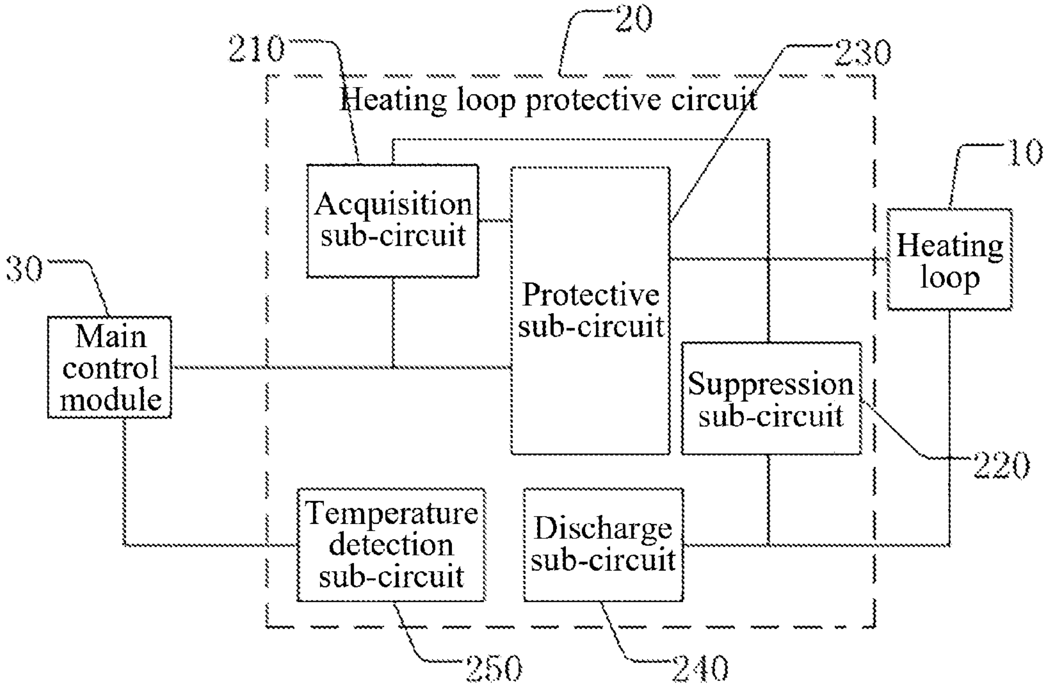
FIG. 1 is a structure block diagram of respiration aiding equipment in the present disclosure.

Referring to FIG. 1, the respiration aiding equipment provided by the present disclosure includes a heating loop 10, a heating loop protective circuit 20 connected to the heating loop and a main control module 30, the heating loop 10 is connected to the heating loop protective circuit 20, and when a short circuit occurs to the heating loop 10, the heating protective circuit performs the short-circuit protection on the heating loop 10. Wherein the heating loop protective circuit 20 is configured to connect to the heating loop 10, and the heating loop protective circuit 20 includes an acquisition sub-circuit 210, a suppression sub-circuit 220, a protective sub-circuit 230 and a discharge sub-circuit 240. The heating loop 10 is generally supplied with power and controlled through the main control module 30, the acquisition sub-circuit 210 is respectively connected to the main control module 30, the protective sub-circuit 230 and the suppression sub-circuit 220, the protective sub-circuit 230 is also connected to the heating loop 10, the heating loop 10 is also connected to the discharge sub-circuit 240, and the main control module 30 may be a main control chip of the respiration aiding equipment or an externally connected main control circuit and not limited herein. The heating loop protective circuit 20 is arranged between the main control module 30 and the heating loop 10, so as to avoid the safety risk caused by instantaneous high voltage touched electric spark.

During the specific implementation, the acquisition sub-circuit 210 collects input voltage of the protective sub-circuit 230 and sends the input voltage to the suppression sub-circuit 220; the suppression sub-circuit 220 clamps the input voltage and releases current through the discharge sub-circuit 240; and the protective sub-circuit 230 performs short-circuit protection when the current is too high. At the same time, this embodiment realizes voltage clamp protection and over-current protection, so that the heating loop 10 avoids high voltage, and realizes the over-current protection function.

Further, the heating loop 10 includes a heating wire H1, a temperature detection module 100 and an identification module IC1; an input end of the heating wire H1 is connected to the protective sub-circuit 230, an output end of the heating wire H1 is connected to a cathode of a first power source, and the temperature detection module 100 and the identification module IC1 are connected to the protective sub-circuit 230 and the suppression sub-circuit 220; wherein the temperature detection module 100 includes a first temperature detection device RV1 and a second temperature detection device RV2, one end of the first temperature detection device RV1, one end of the second temperature detection device RV2 and the identification module IC1 are connected to the protective sub-circuit 230, and the other end of the first temperature detection device RV1, the other end of the second temperature detection device RV2 and a grounding end of the identification module IC1 are connected to an input end of the suppression sub-circuit 220 and the protective sub-circuit 230; wherein the identification module IC1 is specifically an identification chip, which can store temperature data detected by the temperature detection module 100 and upload the temperature data required by the main control module 30.

In this embodiment, the acquisition sub-circuit 210 collects the input voltage of the protective sub-circuit 230 and sends the input voltage to the suppression sub-circuit 220; the suppression sub-circuit 220 clamps the input voltage and releases the current through the discharge sub-circuit 240; and the protective sub-circuit 230 performs short-circuit protection when the current is too high. At the same time, this embodiment realizes voltage clamp protection and over-current protection, so that the heating loop 10 avoids high voltage, and realizes over-current protection function, thereby avoiding the safety risk caused by instantaneous high voltage touched electric spark.

Figure 2:
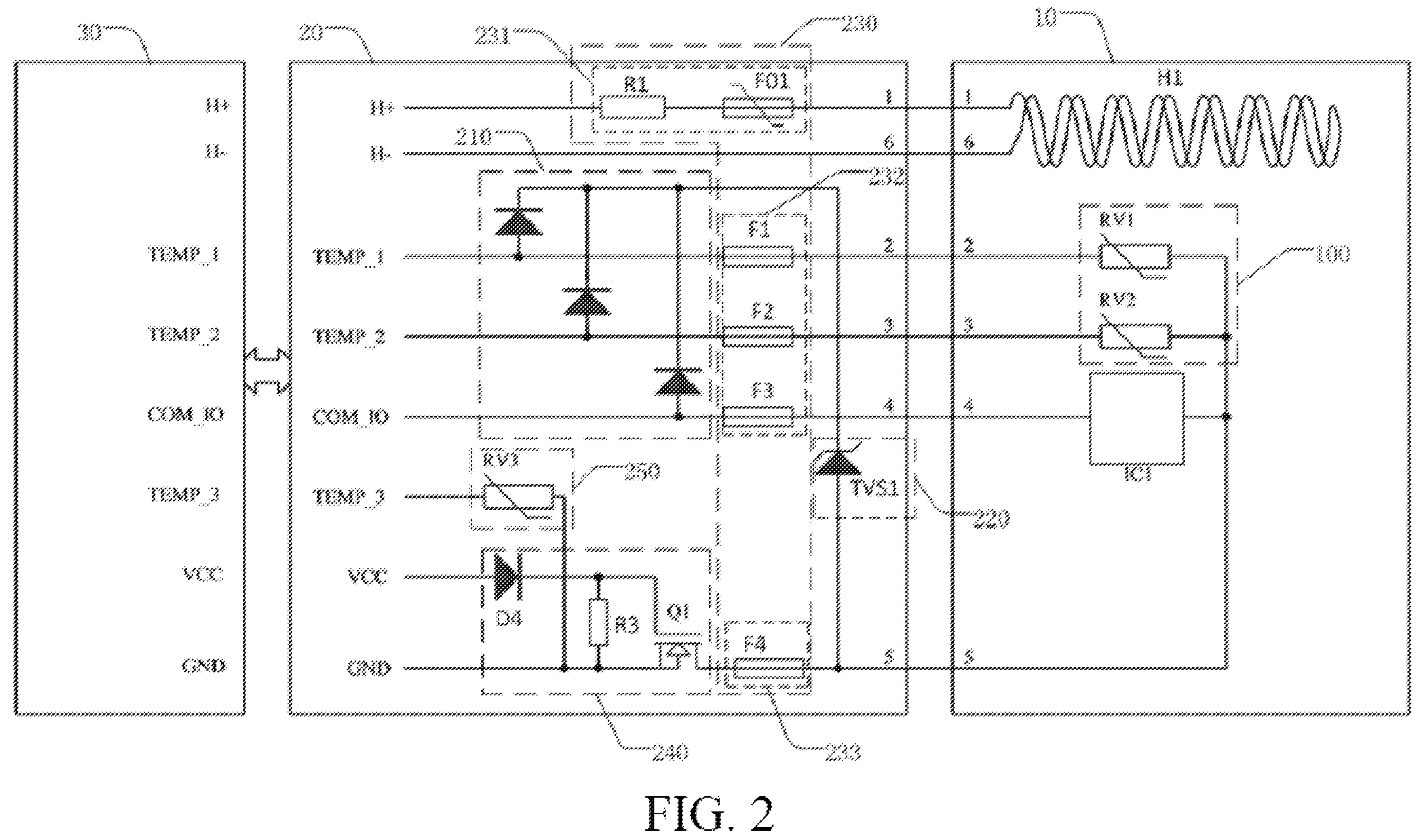
FIG. 2 is a circuit diagram of a first embodiment of respiration aiding equipment in the present disclosure.

Further, referring to FIG. 2, the acquisition sub-circuit 210 includes a first diode D1, a second diode D2 and a third diode D3; an input end of the first diode D1, an input end of the second diode D2 and an input end of the third diode D3 are connected to the protective sub-circuit 230, and collect first input voltage, second input voltage and third input voltage respectively; and an output end of the first diode D1, an output end of the second diode D2 and an output end of third diode D3 are connected to the suppression sub-circuit 220.

The existing heating loop 10 generally includes a plurality of IO ports, which supply power to the heating wire H1, the temperature detection module 100 and the like respectively, or communicate with the identification module IC1, and this embodiment takes six 10 ports as examples for explanation. Specifically, a first 10 port is accessed into the anode of the first power source so as to supply power to the heating wire H1; a second IO port is connected to a cathode of the first power source, so that the heating wire H1 is formed with a loop; the first input voltage supplies power to the first temperature detection device RV1 through a third IO port; the second input voltage supplies power to the second temperature detection device RV2 through a fourth IO port; the third input voltage communicates with the identification module IC1 through a fifth IO port; and a sixth IO port is configured to enable the temperature detection device and the identification module IC1 to ground. When the heating loop 10 is powered on, voltage values of the third IO port, the fourth IO port and the fifth IO port are respectively collected through the first diode D1, the second diode D2 and the third diode D3 and output to the suppression sub-circuit 220, and voltage clamp is realized through the suppression sub-circuit 220, so that a backward heating loop 10 is not burned even the power-on instantaneous voltage is too high, and electric spark is not produced.

Further, please still refer to FIG. 2, in the first embodiment of the present disclosure, the protective sub-circuit 230 includes a first protective unit 231 for performing short-circuit protection on the heating wire H1, a second protective unit 232 for performing short-circuit protection on the temperature detection module 100 of the heating loop 10, and a third protective unit 233 for performing short-circuit protection on the discharge sub-circuit 240; one end of the first protective unit 231 is connected to the input end of the heating wire H1, the other end of the first protective unit 231 is accessed to the first power source, one end of the second protective unit 232 is connected to the acquisition sub-circuit 210 and accessed to the input voltage, the other end of the second protective unit 232 is connected to the temperature detection module 100 and the identification module IC1 of the heating loop 10, one end of the third protective unit 233 is connected to the suppression sub-circuit 220, and the other end of the third protective unit 233 is connected to the discharge sub-circuit 240.

During the specific implementation, in this embodiment, the heating wire H1 is subjected to the over-current protection through the first protective unit 231, when the current is too high, the loop of the heating wire H1 is disconnected through the first protective unit 231, so that the heating wire H1 is powered off, thereby achieving the effect of over-current protection.

Further, the first protective unit 231 includes a first resistance R1 and a first fuse F01; one end of the first fuse F01 is connected to one end of the first resistance R1, the other end of the first fuse F01 is connected to the input end of the heating wire H1, and the other end of the first resistance R1 is connected to the anode of the first power source. The first fuse F01 in this embodiment is a self-recovery fuse, when the heating wire is in short circuit, the resistance of the first fuse F01 will increase, thereby limiting the current in a certain range. After removing the fault, the first fuse F01 will recover the normal state, thereby effectively preventing equipment damage caused by the short circuit of the heating wire.

Further, the second protective unit 232 includes a first protective tube F1, a second protective tube F2 and a third protective tube F3, and the third protective unit 233 includes a fourth protective tube F4; one end of the first protective tube F1 is connected to the input end of the first diode D1 and accessed to the first input voltage; the other end of the first protective tube F1 is connected to the temperature detection module 100; one end of the second protective tube F2 is connected to the input end of the second diode D2 and accessed to the second input voltage; the other end of the second protective tube F2 is connected to the temperature detection module 100; one end of the third protective tube F3 is connected to the input end of third diode D3 and accessed to the third input voltage; the other end of the third protective tube F3 is connected to the identification module IC1; and one end of the fourth protective tube F4 is connected to an anode end of the suppression sub-circuit 220, the temperature detection module 100 and the identification module IC1, and the other end of the fourth protective tube F4 is connected to the discharge sub-circuit 240.

In this embodiment, the first protective tube F1, the second protective tube F2, the third protective tube F3 and the fourth protective tube F4 are fused when the current is great, so as to disconnect the loop and realize the purpose of over-current protection.

Further, the suppression sub-circuit 220 includes a transient voltage suppressor TVS1, a cathode end of the transient voltage suppressor TVS1 is connected to the output end of the first diode D1, the output end of the second diode D2 and the output end of the third diode D3, and an anode end of the transient voltage suppressor TVS1 is connected to one end of the third protective unit 233. In this embodiment, the transient voltage suppressor TVS1 respectively receives voltage collected from the first diode D1, the second diode D2 and the third diode D3, the voltage is kept at a preset value, a three-circuit current is output to the fourth protective tube F4 and output to the discharge sub-circuit 240 through the fourth protective tube F4, and the current is discharged to ground through the discharge sub-circuit 240. It is noted that the preset value of the clamp voltage of the transient voltage suppressor TVS1 may be set according to needs, and it is not limited herein.

Further, the discharge sub-circuit 240 includes a fourth diode D4, a third resistance R3 and a first switch tube Q1, an input end of the fourth diode D4 is accessed into control voltage, an output end of the fourth diode D4 is connected to one end of the third resistance R3 and a control end of the first switch tube Q1, an input end of the first switch tube Q1 is connected to the third protective unit 233, and an output end of the first switch tube Q1 is connected to the other end of the third resistance R3 and grounded.

In this embodiment, a second power source accessed through the fourth diode D4 is output to the control end of the first switch tube Q1, the first switch tube Q1 is a NMOS tube, therefore the control end of the first switch tube Q1 is a grid electrode, the input end of the first switch tube Q1 is a drain electrode/source electrode of the NMOS tube, and the output end of the first switch tube Q1 is the source electrode/drain electrode of the NMOS tube. In this embodiment, the current accessed by the input end of the first switch tube Q1 is discharged to the ground by the output end of the first switch tube Q1, thereby realizing the normal current discharge. Optionally, the first switch tube Q1 may be a PMOS tube or a triode and the like, which only need to realize the current discharge function, and are limited herein.

Further, the heating loop protective circuit 20 further includes a temperature detection sub-circuit 250, which is accessed to the second power source, and an output end of the temperature detection sub-circuit 250 is grounded. Specifically, the temperature detection sub-circuit 250 includes a third temperature detection device RV3, and the temperature detection of the heating loop protective circuit 20 is realized by the third temperature detection device RV3. When the temperature is too high, the power failure is controlled through the main control module 30, so as to avoid losing the protective effect due to high temperature of the heating loop protective circuit 20.

It is noted that the first temperature detection device RV1, the second temperature detection device RV2 and the third temperature detection device RV3 may be temperature sensors, thermistors and the like, which are not limited herein.

Figure 3:
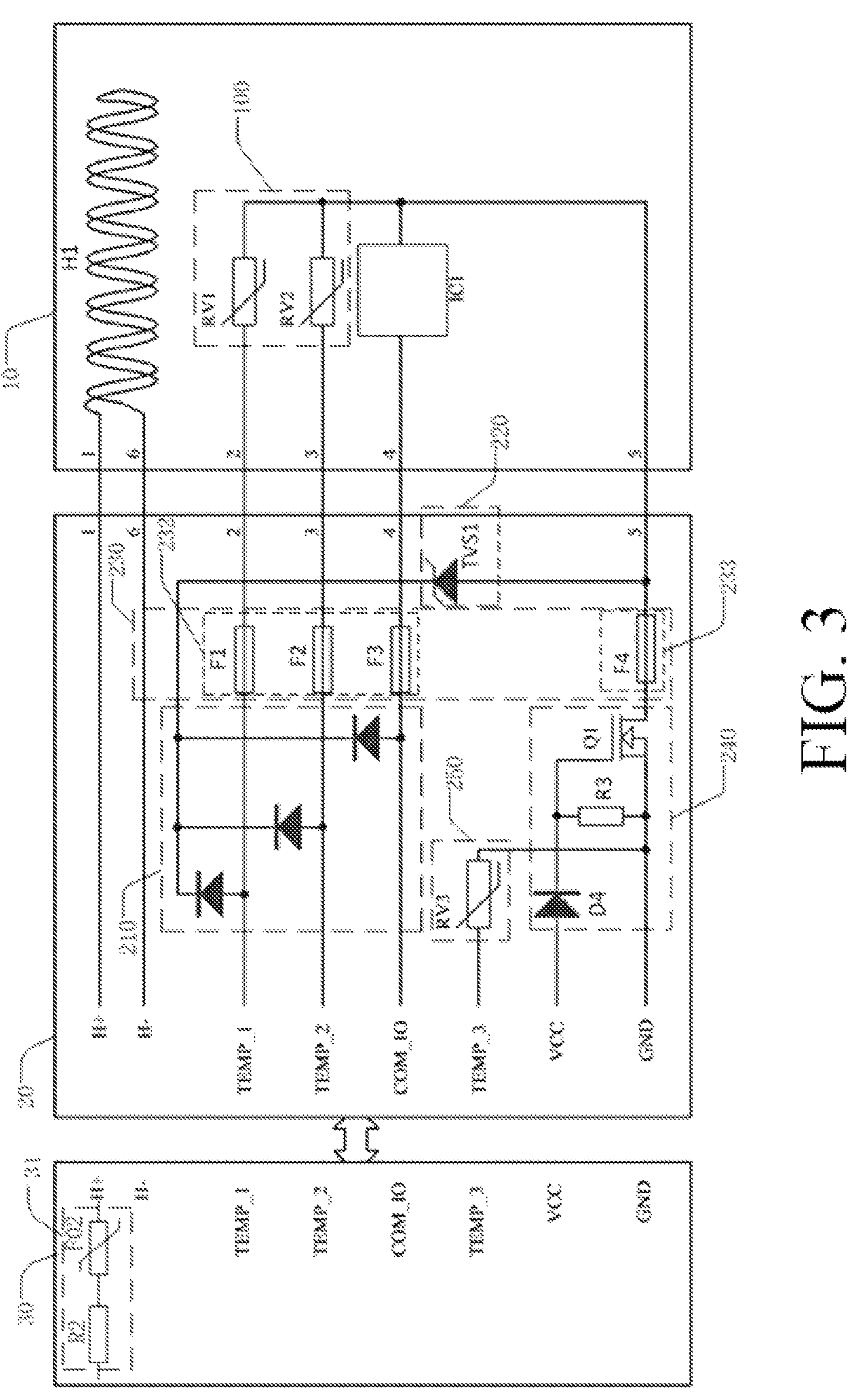
FIG. 3 is a circuit diagram of a second embodiment of respiration aiding equipment in the present disclosure.

Further, referring to FIG. 3, in the second embodiment of the present disclosure, the main control module 30 includes a first protective unit 31 for performing the short-circuit protection on the heating wire, one end of the first protective unit 31 is connected with the output end of the power source, and the other end of the first protective unit 31 is accessed to the input end of the power source; compared with the first embodiment, the first protective unit 31 may be arranged in the main control module 30, the main control module 30 in this embodiment is the main control board of the equipment, namely, the first protective unit 31 may be arranged in the heating loop protective circuit to protect the heating loop or arranged in the equipment to protect the heating loop.

Further, the protective sub-circuit 230 includes a second protective unit 232 for performing the short-circuit protection on the temperature detection module 100 of the heating loop, and a third protective unit 233 for performing the short-circuit protection on the discharge sub-circuit 240; one end of the second protective unit 232 is connected to the acquisition sub-circuit 210 and accessed to the input voltage, the other end of the second protective unit 232 is connected to the temperature detection module 100 and the identification module IC of the heating loop 10, one end of the third protective unit 233 is connected to the suppression sub-circuit 220, and the other end of the third protective unit 233 is connected to the discharge sub-circuit 240. Same as the first embodiment, the protective sub-circuit 230 in this embodiment includes the second protective unit 232 and the third protective unit 233, specifically the function and structure of the second protective unit 232 and the third protective unit 233 are the same as those in the first embodiment and not repeated herein.

Further, the first protective unit 31 includes a second resistance R2 and a second fuse F02; one end of the second fuse F02 is connected to one end of the second resistance R2, the other end of the second fuse F02 is connected to the output end of the power source, and the other end of the second resistance R2 is connected to the input end of the power source. In this embodiment, the power output end connected to the second fuse F02 is the anode of the first power source and equivalent to an input end of the heating wire, in this embodiment, the first protective unit is arranged in the power wire of the main control module 30, and the main control module 30 supplies power to the heating loop through the power wire. Similarly, the second fuse F02 in this embodiment is a self-recovery fuse, when the heating wire is in short circuit, the resistance of the second fuse F02 will increase, thereby limiting the current in a certain range. After removing the fault, the first fuse F01 will recover the normal state, thereby effectively preventing equipment damage caused by the short circuit of the heating wire.

In conclusion, the present disclosure provides respiration aiding equipment, the respiration aiding equipment includes the main control module, the heating loop and the heating loop protective circuit connected to the heating loop, and the heating loop protective circuit includes the acquisition sub-circuit, the suppression sub-circuit, the protective sub-circuit and the discharge sub-circuit; the acquisition sub-circuit collects input voltage of the protective sub-circuit and sends the input voltage to the suppression sub-circuit; the suppression sub-circuit clamps the input voltage and releases current through the discharge sub-circuit; and the protective sub-circuit performs short-circuit protection when the current is too high. In the present disclosure, the over-voltage protection is realized through the voltage clamp in such a manner of monitoring the voltage of the heating loop and suppressing the input voltage through the suppression sub-circuit, and then the over-current protection is realized by protecting the sub-circuit when the circuit current is too high, thereby avoiding the safety risk caused by instantaneous high voltage touched electric spark.

It is understood that those of ordinary skill in the art can make equivalent replacements or changes according to the technical solution and its inventive concept. However, these changes or replacement fall in the protection scope of the claims of the present disclosure.

What is claimed is:

1. Respiration aiding equipment, comprising:

a main control module, a heating loop, comprising a temperature detection module to detect first temperature data of the heating loop, and a heating loop protective circuit connected to the heating loop, wherein the heating loop protective circuit comprises an acquisition sub-circuit, a suppression sub-circuit, a protective sub-circuit, a discharge sub-circuit and a temperature detection sub-circuit to detect second temperature data of the heating loop protective circuit; the protective sub-circuit is connected to the temperature detection module of the heating loop and generates input voltage according to the first detected temperature data, the acquisition sub-circuit collects the input voltage of the protective sub-circuit and sends the input voltage to the suppression sub-circuit; the suppression sub-circuit clamps the input voltage and releases current through the discharge sub-circuit; and the protective sub-circuit performs short-circuit protection when the current is too high;

wherein the discharge sub-circuit comprises a discharging diode, a discharging resistance and a discharging switch tube, an input end of the discharging diode is accessed into control voltage of the main control module, an output end of the discharging diode is connected to one end of the discharging resistance and a control end of the discharging switch tube, an input end of the discharging switch tube is connected to the suppression sub-circuit, and an output end of the discharging switch tube is connected to the other end of the discharging resistance, the temperature detection sub-circuit and grounded.

2. The respiration aiding equipment according to claim 1, wherein the acquisition sub-circuit comprises a first diode, a second diode and a third diode; an input end of the first diode, an input end of the second diode and an input end of the third diode are connected to the protective sub-circuit, and collect first input voltage, second input voltage and third input voltage respectively; and an output end of the first diode, an output end of the second diode and an output end of third diode are connected to the suppression sub-circuit.

3. The respiration aiding equipment according to claim 2, wherein the protective sub-circuit comprises:

a first protective unit for performing short-circuit protection on a heating wire;

a second protective unit for performing short-circuit protection on the temperature detection module of the heating loop;

a third protective unit for performing short-circuit protection on the discharge sub-circuit; and one end of the first protective unit is connected to an input end of the heating wire, the other end of the first protective unit is accessed to a first power source, one end of the second protective unit is connected to the acquisition sub-circuit and accessed to input voltage, the other end of the second protective unit is connected to the temperature detection module and an identification module of the heating loop, one end of the third protective unit is connected to the suppression sub-circuit, and the other end of the third protective unit is connected to the discharge sub-circuit.

4. The respiration aiding equipment according to claim 2, wherein the main control module comprises a first protective unit for performing the short-circuit protection on the heating wire, one end of the first protective unit is connected to an output end of the power source, and the other end of the first protective unit is connected to an input end of the power source.

5. The respiration aiding equipment according to claim 4, wherein the protective sub-circuit comprises a second protective unit for performing the short-circuit protection on the temperature detection module of the heating loop, and a third protective unit for performing the short-circuit protection on the discharge sub-circuit; one end of the second protective unit is connected to the acquisition sub-circuit and accessed to the input voltage, the other end of the second protective unit is connected to the temperature detection module and an identification module of the heating loop, one end of the third protective unit is connected to the suppression sub-circuit, and the other end of the third protective unit is connected to the discharge sub-circuit.

6. The respiration aiding equipment according to claim 3, wherein the first protective unit comprises a first resistance and a first fuse; and one end of the first fuse is connected to one end of the first resistance, the other end of the first fuse is connected to the input end of the heating wire, and the other end of the first resistance is connected to an anode of a first power source.

7. The respiration aiding equipment according to claim 3, wherein the second protective unit comprises a second resistance and a second fuse; and one end of the second fuse is connected to one end of the second resistance, the other end of the second fuse is connected to the output end of the power source, and the other end of the second resistance is connected to the input end of the power source.

8. The respiration aiding equipment according to claim 3, wherein the second protective unit comprises a first protective tube, a second protective tube and a third protective tube; one end of the first protective tube is connected to the input end of the first diode and accessed to first input voltage; the other end of the first protective tube is connected to the temperature detection module; one end of the second protective tube is connected to the input end of the second diode and accessed to second input voltage; the other end of the second protective tube is connected to the temperature detection module; one end of the third protective tube is connected to the input end of third diode and accessed to third input voltage; and the other end of the third protective tube is connected to the identification module.

9. The respiration aiding equipment according to claim 6, wherein the first fuse is a self-recovery fuse.

10. The respiration aiding equipment according to claim 7, wherein the second fuse is a self-recovery fuse.

11. The respiration aiding equipment according to claim 5, wherein the second protective unit comprises a first protective tube, a second protective tube and a third protective tube; one end of the first protective tube is connected to the input end of the first diode and accessed to first input voltage; the other end of the first protective tube is connected to the temperature detection module; one end of the second protective tube is connected to the input end of the second diode and accessed to second input voltage; the other end of the second protective tube is connected to the temperature detection module; one end of the third protective tube is connected to the input end of third diode and accessed to third input voltage; and the other end of the third protective tube is connected to the identification module.

* * * * *